United States Patent [19]

Goldenberg

[11] 4,348,376

[45] Sep. 7, 1982

[54] TUMOR LOCALIZATION AND THERAPY WITH LABELED ANTI-CEA ANTIBODY

[76] Inventor: Milton D. Goldenberg, 11837 Gainsborough Rd., Potomac, Md. 20854

[21] Appl. No.: 126,262

[22] Filed: Mar. 3, 1980

[51] Int. Cl.³ .............................................. A61K 49/00
[52] U.S. Cl. ......................................... 424/1; 128/1.1; 128/659; 424/9
[58] Field of Search ................. 424/1, 9; 128/659, 1.1

[56] References Cited

U.S. PATENT DOCUMENTS

| | | | |
|---|---|---|---|
| 3,927,193 | 12/1975 | Hansen et al. | 424/1 |
| 4,160,817 | 7/1979 | Bucovaz et al. | 424/1 |
| 4,174,385 | 11/1979 | Reid | 424/1 |
| 4,211,766 | 7/1980 | Björklund | 424/12 |

OTHER PUBLICATIONS

Mach et al., *Europ. J. Cancer, Suppl.* 1, 113 (1978).
Spar, *Sem. Nucl. Med.* 6, 379 (1976).
Emrich, *Dtsch. Med. Wschr.*, 104, 153 (1979).
Lee et al., *Scand. J. Immunol.*, 8 (Suppl. 8), 485 (1978).
Heyderman, *Scand. J. Immunol.*, 8 (Suppl. 8), 119 (1978).
Goldenberg et al., *N. Eng. J. Med.*, 298, 1384 (1978).
Hawthorne et al., *J. Med. Chem.*, 15, 449 (1972).
Order, *Radiology*, 118, 219 (1976).
Ettinger et al., *Cancer Treat. Rep.*, 63, 131 (1979).
Order et al., *Int. J. Radiation Oncology Biol. Phys.*, 6, 703 (1980).
Ballou et al., *Science*, 206, 844 (1979).
Pressman, *Cancer Res.*, 40, 2960 (1980).
Bale et al., *Cancer Res.*, 40, 2965 (1980).
Order et al., *Cancer Res.*, 40, 3001 (1980).
McIntire et al., *Cancer Res.*, 40, 3083 (1980).

*Primary Examiner*—Christine M. Nucker
*Attorney, Agent, or Firm*—Millen & White

[57] ABSTRACT

Improved methods are provided for using radiolabeled antibodies to carcinoembronic antigen (CEA) to locate, diagnose and stage CEA-containing tumors by external photoscanning, whereby significantly increased resolution, convenience and/or efficiency of operation may be achieved. A method is provided for using highly specific radiolabeled anti-CEA antibodies for tumor therapy. An injectable composition and radiolabeled antibodies are provided for use in the method of the invention.

39 Claims, No Drawings

TUMOR LOCALIZATION AND THERAPY WITH LABELED ANTI-CEA ANTIBODY

BACKGROUND OF THE INVENTION

It is known that radiolabeled antibodies to carcinoembronic antigen (CEA) can be used to localize tumors. U.S. Pat. No. 3,927,193, to Hansen et al, discloses such a method, but provides examples of its use only in animals. The method described in this patent does not explain how tumors may be visualized in a situation where radioactivity is also present in other sites of the body, such as blood, other body fluids and certain tissues, particularly heart and liver, which can prevent precise discrimination of the radioactivity associated with the sites of tumor. Early clinical studies reported by Reif et al, *J. Surg.Oncol.*, 6, 133 (1974) and Mach et al, *Europ. J. Cancer, Suppl.* 1, 113 (1978) failed to show tumor localization in humans with radioactive anti-CEA antibodies.

Goldenberg et al, in an article in the *New England Journal of Medicine*, 298, 1384 (1978), reported success in clinical trials of tumor detection and localization by scintillation scanning of patients receiving radiolabeled antibodies to CEA. In that reference, it was noted that there was a problem in both animal and human studies in distinguishing specific radioantibody activity from blood-pool background activity, and that special scanner subtraction techniques with other radionuclides were considered essential for unequivocal tumor localization using this method. The antibody preparation used in the reference was 70% immunoreactive with CEA. The reference further notes that the absence of CEA in normal hamster tissues precludes extrapolation to man, in whom the antigen usually circulates in increased levels in patients with cancer, and is present in lesser quantities in certain normal tissues. The subtraction technique used to permit localization using this scintigraphic method involved injection of Tc-99m-pertechnetate and Tc-99m-labeled human serum albumin prior to each imaging scan. The data obtained were stored in a minicomputer capable of generating digital images of the labeled antibody alone, the Tc-99m labeled species together, and sums and differences of these various values.

Even this most recent and successful tumor localization and detection process has certain disadvantages which limit its resolution, it efficiency and its practicability. The use of a different radionuclide attached to a carrier having kinetics of transport and distribution different from an antibody in the subtraction technique used to distinguish tumor localized antibody from background activity is not an ideal procedure. Furthermore, the need to inject these materials prior to each photoscan is an inconvenience, it not an ideal procedure, and exposes the patient to increased levels of radioactivity. U.S. Pat. No. 3,927,193 teaches that the anti-CEA antibody should not be labeled to a degree which might interfere with the activity of the antibody, a limitation which was not questioned in the later references discussed above. However, this limits the resolution of the method and requires larger quantities of antibody for image detection.

Tumor radiotherapy using labeled antibodies has been suggested by many, and an indication of its success in a single multimodal therapeutic clinical use is reported by Order, *Radiol.*, 118, 219 (1976). The use of boron-labeled antibodies in therapy is reported by Hawthorne et al., *J. Med. Chem.*, 15, 449 (1972), but the combined incorporation of boron and a radioisotope for localization is not suggested.

A need therefore continues to exist for a method of tumor detection and localization which can achieve high resolution and which avoids the aforementioned disadvantages.

OBJECTS OF THE INVENTION

Accordingly, it is an object of the present invention to provide a method of tumor localization and detection which achieves high resolution without the necessity of repeated injection of other radioactive material for computer subtraction of background activity.

Another objective of the present invention is to provide an antibody for tumor detection and localization having a high specific activity and a high specificity for CEA, thereby improving the resolution of scintigraphic tumor localization and detection methods.

A further object of the invention is to provide a method of tumor radiotherapy wherein a radiotherapeutically effective radioisotope is concentrated at the site of tumor growth by virtue of its attachment to an antibody which is highly specific to carcinoembronic antigen.

Upon further study of the specification and appended claims, further objects and advantages of this invention will become apparent to those skilled in the art.

SUMMARY OF THE INVENTION

The foregoing objects are achieved by providing, in a method for determining the location of a tumor which either produces or is associated with carcinoembryonic antigen (CEA), which comprises injecting a subject parenterally with an antibody specific to CEA and radiolabeled with a pharmacologically inert radioisotope capable of detection using a photoscanning device and subsequently scanning the subject with said device to determine the location of the resultant uptake of said antibody by said tumor; the improvement which comprises concurrently injecting said subject with normal immunoglobulin from the same or different species as that used to prepare said specific antibody, said normal immunoglobulin being radiolabeled with a different radioisotope of the same element used to label the specific antibody and emitting at an energy capable of independent detection using said photoscanning device, the level of activity of the labeled normal immunoglobulin being used to determine the distribution of background activity due to non-targeted specific antibody, said distribution being subtracted from the total activity of specific antibody whereby the activity of substantially only the targeted tumor-associated antibody is determined.

The invention further provides an improvement in the foregoing general method which comprises using as said anti-CEA antibody a substantially monospecific antibody having a CEA-specific immunoreactivity prior to labeling of at least 70% and a cross-reactivity of other antigens of less than 15%, said antibody being radiolabeled to an extent sufficient to reduce its CEA-specific immunoreactivity by from 5 to 33%. An antibody and an injectable composition suitable for use in the foregoing method are provided, as are methods of tumor radiotherapy using radiolabeled anti-CEA antibody.

DETAILED DISCUSSION

Antibodies specific to CEA may be produced by a variety of methods known in the art, as reported inter alia in Primus et al, *J. Immunol.*, 118, 55 (1977); Goldenberg et al, supra; Primus et al, *Cancer Res.*, 37, 1544 (1977); and Goldenberg et al, in "Immunodiagnosis of Cancer, Part I", Herberman et al, Eds., pages 265-304 (Marcel Dekker, Inc., New York & Basel, 1979).

As taught in the above references, anti-CEA antibodies may be purified by a variety of techniques, including affinity chromatography. In this technique, the use of bound purified CEA will retain on the column antibodies specific to any of the antigenic determinants on the CEA antigen. Additional purification may be achieved by passing an anti-CEA antibody mixture through one or more columns having bound antigens with which some components of the heterogenous antibody mixture are cross-reactive. This may be done subsequent to, but preferably prior to CEA purification. The resultant antibodies have a high CEA-specific immunoreactivity, often approaching or even exceeding 70%, with a cross-reactivity of less than 15%.

It is particularly advantageous to use antibodies having a high CEA-specific immunoreactivity for tumor localization. High specificity means that a high proportion of the labeled antibody will be targeted at tumor sites and a small proportion will be distributed in a non-targeted manner. A smaller quantity of labeled antibody can therefore be used, reducing the subject's exposure to radiation, and the lower level of background radiation due to non-targeted antibody will improve resolution. This in turn means that smaller tumors may be detected that are often difficult or impossible to detect by any other procedure.

In addition to the aforementioned methods of producing highly specific antibodies, it is advantageous to use hybridization techniques to produce monoclonal, hybridoma-derived antibodies for use in the present method. Monoclonal anti-CEA antibodies may be produced by challenging a rodent, e.g., a mouse, or a subhuman primate, e.g., a monkey, with purified CEA, resulting in the production of anti-CEA antibodies in the mouse or monkey lymph or spleen cells. The mouse or monkey is sacrificed and its lymph or spleen cells are grown in cell culture. Rodent or human myeloma cells are established in tissue culture or in appropriate animal methods. These myeloma cells are hybridized or fused with the mouse or monkey spleen or lymph cells using a fusing agent, e.g., Sendai virus, lysolecithin or polyethylene glycol, permitting chromosomes from the different cells to unite in a single cell. These hybrid cells are selected and individual cells from the hybrid population are cloned. Cells producing the desired anti-CEA antibody are then selected and the pure monoclonal cell population is cultivated in vitro or in an animal to produce tumors which produce the desired monoclonal antibody. The antibody is harvested from the culture fluid or from the ascites fluid of the animal.

Hybridoma-derived monoclonal anti-CEA antibodies are substantially mono-specific for CEA, having a CEA-specific immunoreactivity of at least 90% and a cross-reactivity to other antigens of less than 10%. Where the CEA used to challenge the animal and raise the anti-CEA antibody is itself a highly purified material, these monoclonal anti-CEA antibodies are among the most highly immunospecific antibodies obtainable by present techniques, and they are the preferred antibodies for use in tumor localization.

Monoclonal antibodies from the immunoglobulin G (IgG) fraction are obtained by the prsent method, and are used to prepare the fragments used for tumor detection, localization and therapy according to this invention. The IgM monoclonal antibodies of Koprowski, U.S. Pat. No. 4,172,124, are unsuitable for use in the present method.

Purified anti-CEA antibodies may be radiolabeled by any of several techniques known to the art. A wide range of antibody labeling techniques are disclosed in Feteanu, "Labeled Antibodies in Biology and Medicine", pages 214-309 (McGraw-Hill Int. Book Co., New York et al, 1978). The introduction of various metal radioisotopes may be accomplished according to the procedures of Wagner et al, *J. Nucl. Med.*, 20, 428 (1979); Sundberg et al, *J. Med. Chem.*, 17, 1340 (1974); and Saha et al, *J. Nucl. Med.*, 6, 542 (1976). The foregoing are merely illustrative of the many methods of radiolabeling proteins known to the art, the latter two being preferred for scintigraphy.

Among the radioisotopes used, gamma-emitters, position-emitters, x-ray-emitters and fluorescence-emitters are suitable for localization and/or therapy, while beta-emitters and alpha-emitters may also be used for therapy. Suitable radioisotopes for labeling antibodies include Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

An especially preferred labeling technique involves labeling with either iodine-131 (I-131) or iodine-123 (I-123) using an oxidative procedure wherein a mixture of radioactive potassium or sodium iodide and the antibody is treated with chloramine-T, e.g., as reported by Greenwood et al, *Biochem. J.*, 89, 114 (1963) and modified by McConahey et al, *Int. Arch. Allergy Appln. Immunol.*, 29, 185 (1969). This results in direct substitution of iodine atoms for hydrogen atoms on the antibody molecule, presumably on tyrosine residues, possibly also on tryptophane and even on phenylalanine residues, depending on the proportions of reagents and the reaction conditions.

While the vast majority of investigators had considered that the direct introduction of more than 1.5-2 iodine atoms per antibody molecule by chemical substitution is disadvantageous, it has now been found that the introduction of an average of at least 2.5, and preferably at least 5 iodine atoms per antibody molecule is advantageous, where the antibody is highly CEA-specific prior to labeling. In this case, even a reduction of the antibody specificity of from 5 to 33% as a consequence of high labeling is overcompensated by the advantage of high activity, permitting the use of substantially smaller quantities of labeled antibody. As noted above, the use of highly specific antibodies of high activity results in efficient localization and increased resolution. This balancing of increased activity with reduced specificity is advantageous with up to an average of 10 atoms of iodine per antibody molecule, after which the reduction in specificity outweighs the advantage of high activity. However, other methods of radiolabeling may achieve still higher activity without reduction of specificity by more than 33%. A further improvement may be achieved by effecting radiolabeling in the presence of CEA, to insure that the antigen binding site on the antibody will be protected. The antigen is separated after labeling.

Normal immunoglobulin from either the same or a different species as that used to produce the anti-CEA antibodies is used for the improved subtraction technique of the present invention. Standard techniques known to the art are used to isolate the normal immunoglobulin or commercially available material may be used, and the labeling may be effected in the same manner as that used to label anti-CEA antibodies.

In the subtraction method of the invention, anti-CEA antibody is labeled with a radioisotope and normal immunoglobulin from the same or different species as that used to produce the antibody is labeled with a different radioisotope of the same element. The pairs of radioisotopes used must be capable of independent detection using a photoscanning device. If both isotopes are gamma-emitters, they must emit at a sufficiently different energy as to be separately detectable. If one of the isotopes is a gamma-emitter and the other is a position-emitter, independent detection is facilitated. Advantageously, the more intense emitter will be used to label the anti-CEA antibody.

In the reported successful noninvasive radioimmunodetection of cancer in humans of Goldenberg et al, *N. Eng. J. Med.*, 298, 1384 (1978), a subtraction technique was shown to be necessary for successful localization. However, the subtraction technique used was substantially different from that of the present invention. In the reference process, radioiodinated anti-CEA antibody was injected, and technetium-99m-labeled human serum albumin and technetium-99m-pertechnetate were injected intravenously before each imaging scan. Images were obtained with a gamma-scintillation camera and the data obtained were stored in a minicomputer. The ratio of I-131 activity to Te-99m-activity in non-target areas provided a standard of comparison for background non-localized antibody activity. This in turn permitted a determination of non-targeted specific antibody activity at other locations, which was then subtracted from the total specific antibody activity to yield a value for the activity of localized, targeted antibody.

This invention provides an alternative subtraction technology not evident in earlier work which improves the tumor-localizing photoscanning process by using normal immunoglobulin labeled with a different radioisotope of the same element used to label the specific antibody. Thus, an independently detectable species having substantially the same distribution and kinetic properties is used to determine the background level of antibody activity. A corollary advantage of the present process is the possibility of substantially earlier tumor imaging than with other agents and methods, since the radiolabeled antibody and the radiolabeled normal immunoglobulin can be injected concurrently, although this is not essential. Additional injections of non-specific radiolabeled species for background activity determinations are also unnecessary, in contrast to the prior art procedure using radiolabeled human serum albumin, pertechnetate or other such interstitial and blood-pool radiopharmaceutical agents.

In contrast to earlier known procedures, which permit tumor localization usually only after 24 hours following administration of the radiolabeled specific antibody, the present improved subtraction technique permits tumor detection and localization within less than 24 hours after concurrent administration of radiolabeled anti-CEA antibody and radiolabeled normal immunoglobulin. Tumor localization may be achieved as early as two hours after injection of the antibody/immunoglobulin pair, with improved resolution of 6, 12, 18 and 24 hours after administration.

The use of an anti-CEA antibody which is substantially monospecific, having a CEA-specific immunoreactivity prior to labeling of at least 70% and a cross-reactivity to other antigens of less than 15%, the antibody being radiolabeled to an extent sufficient to reduce its CEA-specific immunoreactivity by from 5 to 33%, makes tumor localization possible without the use of a subtraction technique. This is especially the case where the monospecific antibody is a monoclonal anti-CEA antibody. When the substantially monospecific antibody has a CEA-specific immunoreactivity prior to labeling of at least 80%, and a cross-reactivity of less than 10%, especially when the antibody is monoclonal, increased resolution may be achieved. As noted above, this is due to the heretofore unappreciated fact that high labeling of a highly specific antibody permits the use of a smaller quantity of antibody which is localized with unexpectedly high efficiency in tumor sites. Background activity due to non-targeted antibody is therefore reduced.

Of course, the combination of highly labeled, highly specific antibody with the improved subtraction technique of this invention leads to even greater resolution. In a preferred embodiment, substantially monospecific anti-CEA antibody is radiolabeled with I-131 or I-123, an average of at least 2.5 and preferably from 5 to 10 atoms of iodine per antibody molecule being introduced, and the resultant highly labeled monospecific antibody is injected according to the present method. The use of monoclonal anti-CEA antibody radiolabeled with I-131 or I-123 to an average iodine content of at least 2.5 and preferably from 5 to 10 atoms per antibody molecule is also preferred.

Further improved resolution is achieved by using a radiolabeled purified normal immunoglobulin for the reference substance in the subtraction techique. Normal globulin is a mixture of globulins, some of which may bind to the specific antigen to which the radioactive antibody is directed. Therefore, it is desirable to purify the normal globulin to be used as a subtraction agent so as to remove any reactivity to the specific marker in question, and one such purification method is to adsorb the normal immunoglobulin with the specific antigen, preferably on a solid adsorbent, so that the globulins reacting with the antigen would be retained on the column and the materials passing throuhgh would be more suitable for labeling as a non-specific subtraction agent. Monoclonal non-specific immunoglobulin or myeloma protein itself would also have the desired purity for labeling and use as subtraction agents.

When the subtraction technique of the invention is used, the balance between high activity and high specificity can be struck more on the side of a somewhat lower extent of radiolabel with a correspondingly lower reduction in CEA-specific immunoreactivity of the antibody. Again, the higher the CEA-specific immunoreactivity, the higher the labeling can be while still preserving an advantageous balance of antibody properties. Thus, a substantially monospecific antibody having a CEA-specific immunoreactivity of at least 70%, preferably at least 80%, and a cross-reactivity of less than 15%, preferably less than 10%, can be labeled with I-131 or I-123 to an extent of from 2.5, but preferably from 5 to 10 atoms of iodine per antibody molecule while still retaining a sufficient CEA specificity after labeling to permit highly efficient localization.

The use of the present method, either without but preferably with the improved subtraction technique, permits either continuous, repeated to occasional monitoring of tumor locations. This has particular advantages in conjunction with the diagnosis and staging of tumors prior to surgery. In addition, the method is useful during and after surgery as an indication of the extent to which complete tumor removal has been achieved. In case of metastasis, especially where there has been a proliferation of small, diffuse metastases, the high resolution of the present method permits identification of target areas for post-operative therapy. This can be effected using the therapeutic method of this invention or other known techniques, e.g., chemotherapy, radiation treatments, or multimodal therapies.

Radiolabeled CEA-specific antibodies are effective for tumor therapy. After it has been determined that labeled anti-CEA antibodies are localized at tumor sites in a subject, a higher dose of labeled antibody, generally from 25 to 250 mCi, and preferably from 50 mCi to 150 mCi per dose is injected. Injection may be intravenous, intraarterial, intralymphatic, intrathecal, or intracavitary, and may be repeated.

A variety of radionuclides are useful for therapy, and they may be incorporated into the anti-CEA antibody by the labeling techniques discussed above. The preferred therapeutically effective radionuclide is I-131.

The therapeutic method of this invention also advantageously makes use of highly specific anti-CEA antibody, preferably an antibody which is substantially monospecific to CEA, having a CEA-specific immunoreactivity of at least 70%, preferably 80%, and a cross-reactivity to other antigens of less than 15%, preferably less than 10%. Monoclonal anti-CEA antibodies are preferred because of their high specificity.

Therapy using radiolabeled CEA-specific antibody is advantageously used as a primary therapeutic treatment, in combination with other therapies, e.g., radiation and chemotherapy, and as an adjunct to surgery. Where there may be small metastases which cannot be surgically removed or which may escape detection, the radiotherapeutic method of the invention provides a potent weapon capable of seeking out and destroying these tumors.

A further aspect of the present invention relates to the use of antibodies containing both a radioisotope label and an addend containing significant numbers of boron atoms, having at least the 20% natural abundance of boron-10 isotope. The boron-containing addend may be introduced by a variety of methods, preferably by coupling the antibody with a boron-rich coupling agent, such as the diazonium ion derived from 1-(4-aminophenyl)-1,2-dicarbacloso-dodccaboranc(12), according to the method of Hawthorne et al, *J. Med. Chem.*, 15, 449 (1972). The boron-10-containing antibody is then radiolabeled according to one or more of the above procedures to produce an antibody containing both one or more radiolabels for tumor localization and/or therapy and a high content of boron-10 atoms for the absorption of thermal neutrons. Boron-10 absorbs thermal neutrons and the activated nucleus decays rapidly to Lithium-7 and an alpha-particle. These resultant alpha-particles are cytotoxic, and their production in tumor cells kills the cells and causes tumor reduction.

Combination of a boron addend with one or more radiolabels on a highly marker-specific antibody provides for the first time a single agent which functions as a multimodal tumor therapeutic agent. The rapid and specific localization of these doubly labeled antibodies at the site of a tumor permits a rapid and precise definition of the areas where neutron irradiation should be focused. Moreover, as tumor cells are destroyed by the combined effects of radiation from the radiolabel and neutron-activated boron-10 emissions, and the killed tumor cells are eliminated, the progress of the radiotherapeutic treatment may be monitored by measurement of localized, radiolabeled antibody or other tumor detection methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever, in the following examples, all temperatures are set forth uncorrected in degrees Celsius; unless otherwise indicated, all parts and percentages are by weight.

EXAMPLE 1

Preparation of $^{131}$I-anti-CEA IgG (goat)

(a) CEA is obtained in high purity from hepatic metastasis of colonic carcinoma by the method of Newman et al., *Cancer Res.*, 34, 2125 (1974).

(b) Purified CEA, 0.5 mg dry weight, is dissolved in 2 ml of water containing 2 mg methylated bovine serum albumin (Sigma) and the CEA solution is emulsified with an equal volume of complete Freund's adjuvant (Difco).

Equal portions of the CEA inoculum are injected subcutaneously into two separate sites on the neck of a healthy goat. Injections are administered bi-weekly until radioimmunoassay of antiserum collected 14 days after the last injection shows an anti-CEA titer of greater than 1:10$^6$.

Blood is then collected aseptically from the goat, transferred to pyrogen-free centrifuged tubes and centrifuges. The anti-CEA serum is stored at −20° C.

The complement of the goat anti-CEA serum is inactivated by incubation at 56° C. for one hour, and freed of anti-blood group activity by repeated mixing with washed, packed type AB human RBC's with a serum/RBC ratio calculated from the hemagglutination assay, until no further hemagglutination activity can be detected. The adsorbed anti-CEA serum is then dialyzed against several volumes of 0.1 M pH 7.0 phosphate buffer (PO$_4$).

(c) A colon carcinoma antigen-III (CCA-III) immunoadsorbent is prepared by conjugating the 60,000 MW fraction of the perchloric acid extracts of normal lung to cyanogen bromide-activated Sepharose 4 B (Pharmacia Fine Chemicals, Inc.), using conventional techniques. The conjugation is allowed to proceed overnight at 4° C. with gentle stirring. The CCA-IIIimmunoadsorbent is washed with 0.05 M, pH 8.4, borate buffer and resuspended in 4 volumes of 1 M 2-aminoethanol in 0.1 M, pH 8.0 phosphate buffer. The slurry is mixed for one hour at room temperature, filtered and washed with PO$_4$.

A CCA-III immunoadsorbent column is prepared, precycled with 2 ml of 10% (v/v) normal goat serum (Gibco), and with approximately one column volume of the chaotropic agent 3 M ammonium thiocyanate, and re-equilibrated with 0.1 M pH 7.0 phosphate buffer.

The CCA-III-immunoadsorbent column is inserted into an automated chromatographic system and the entire system is thoroughly washed with apyrogenic, sterile PO$_4$. The buffer reservoirs are replaced with reservoirs containing the chaotropic agent and dialysate.

The adsorbed anti-CEA serum is diluted with PO$_4$ to a volume which is ⅔ that of the void volume of the column and contains an appropriate quantity of antiserum for one cycle through the column. This volume of diluted antiserum is applied and washed into the column with sufficient PO$_4$ to give a total volume of one column void volume. The antiserum is allowed to incubate at room temperature for 20 minutes, then the specific anti-CEA serum, unadsorbed fraction, is eluted from the column with PO$_4$. The column is regenerated by elution with 1.5 to 2 column volumes of 3 M ammonium thiocyanate in PO$_4$ and with 3 to 4 column volumes PO$_4$. The system automatically starts the next cycle by applying a second aliquot of anti-CEA serum. The number of cycles is set to process the entire lot of antiserum.

An aliquot of the anti-CEA serum is concentrated to the original volume of the antiserum and retested by immunodiffusion. The antiserum is tested against reference CEA, a CCA-III preparation, and normal human tissue extracts and plasma. If the antiserum has a positive reaction against the CCA-III preparation, plasma or any normal human tissue extracts, it is recycled with the CCA-III immunoadsorbent column.

(d) A CEA-immunoadsorbent column is prepared by conjugating purified CEA to cyanogen bromide-activated Sepharose 4B by a coupling procedure identical to that of the CCA-III immunoadsorbent, preparing, precycling and equilibrating a column as in part (c).

The CEA-immunoadsorbent column is introduced into the automated chromatographic system and thoroughly washed with apyrogenic PO$_4$. The quantity of anti-CEA serum to be applied with each cycle is calculated on the basis of the radioimmunoassay titration, the sample of antiserum is diluted, applied and incubated as with the CCA-III immunoadsorbent column. The serum protein including all non-reactive immunoglobulins are eluted from the column with PO$_4$ and are collected as the unadsorbed fraction.

The specific anti-CEA IgG is dissociated and eluted from the column with 3 M ammonium thiocyanate in PO$_4$ and is collected as the adsorbed fraction. In order to remove all traces of the ammonium thiocyanate, the adsorbed fraction is subjected to in-line dialysis by the use of hollow fiber dialysis units (Amicon or BioRad) against 1 M urea and 10% glycerol in PO$_4$. An alternate procedure for dissociation of specific antibody uses guanidine HCl as a chaotropic agent and Sephadex G25 gel filtration chromatography for desalting.

The adsorbed fraction is concentrated at 4° C. by ultrafiltration with PM 30 membranes (Amicon) to a volume facilitating gel filtration chromatography, e.g., a lot of 100 ml of anti-CEA serum is concentrated to approximately 20 ml. The concentrate is dialyzed against 4 changes, 4 hours each, of 100 volumes of 50 mM, pH 7.5, phosphate-buffered saline (PBS). The anti-CEA IgG preparation is sterile filtered into a sterile, pyrogen-free serum vial. An aliquot is reserved for quality control testing by RIA and immunodiffusion.

(e) A Sephacryl S-200 (Pharmacia) column is prepared by washing the gel 5 times with sterile, non-pyrogenic 50 mM, pH 7.5, PBS. The columns are dry-heat sterilized, 180° C. for 3 hours. The column sizes used are 2.6×90 cm or 5.0×90 cm depending on the lot size of the antibody. The prepared column is placed in a refrigerated unit or cold room, equilibrated to 4° C. and thoroughly washed with sterile 50 mM PBS. The column is attached to a U.V. monitor and calibrated with commercial normal goat IgG (Pentex), 50 mg in 20 ml for a 5×90 cm column and 20 mg in 5 ml for the 2.6×90 cm column. It is then washed with three column volumes of PBS.

The lot of goat anti-CEA IgG is applied to the column and eluted with PBS at a flow rate of 6 ml/cm$^2$/hr. The fractions containing IgG protein are pooled and concentrated to approximately 5 mg IgG protein/ml, $E^{1\%}_{1cm}=14$ at 280 mμ, dialyzed against PBS, sterile filtered with 0.2 micron Millex units (Millipore) and stored refrigerated in one ml aliquots, approximately 5 mg IgG protein/ml, with sodium azide as a biostatic agent.

(f) Goat anti-CEA IgG, 20 μg IgG per mCi $^{131}$I, is injected into a radionuclide vial containing $^{131}$I (Amersham-Searle).

Chloramine-T and sodium metabisulfite solutions are prepared by the injection of 5 ml of sterile pyrogen-free 0.5 M pH 7.5 phosphate buffer into each of two vials containing 10 mg of chloramine-T and 50 mg of bisulfite, respectively. Chloramine-T solution is injected, 10 μg/mCi $^{131}$I, into the radionuclide vial. Sodium metabisulfite solution, 5 times the amount of Chloramine-T, is injected into the vial exactly 90 seconds after the Chloramine-T. The mixture is removed from the reaction vial with a sterile syringe, the reaction vial is rinsed twice with 1% normal human serum albumin, and the rinses combined with the reaction mixture.

The sample of $^{131}$I-anti-CEA IgG is applied to a PD-10 Sephadex G-25 column which is pre-equilibrated with 1% normal human serum albumin in PBS, eluted with approximately 4.5 ml of 1% normal human serum albumin in PBS, monitored with a shielded gamma detector (Eberline), collected and diluted to a predetermined concentration for storage and use.

The resultant $^{131}$I-anti-CEA IgG has an average of from 3 to 7 atoms of iodine per antibody molecule. Random aliquots from each batch are separately tested for sterility, pyrogenicity, toxicity and other quality control variables.

EXAMPLE 2

Preparation of monoclonal $^{131}$I-anti-CEA IgG

Female, 6-month-old, Balb/C mice are injected with 10-100 μg carcinoembryonic antigen intraperitoneally, whereby the CEA is mixed in an equal volume (10-100 μl) of incomplete Freund's adjuvant. This is repeated one week later, and again two weeks later, but lastly, using the intravenous route without adjuvant. Three to four days later, the mice are killed by cervical dislocation. The optimum time for obtaining antibody against a given antigen varies with the antigen, the route of administration, and the timing of immunization, as well as the interval between the last booster injection and the removal of the spleen cells.

The spleens are removed and placed in 60 mm Petri dishes containing either serum-free medium or Dulbecco's Modified Eagle's Medium (DMEM) with 20% fetal calf serum, at room temperature, and minced with scissors to disperse the cells. The cells are further liberated by agitation for 1-2 min on a Vortex mixer. The spleen cells are removed to a conical centrifuge tube and pelleted at 1,000 rpm in an IEC-MS2 centrifuge, the supernatant is removed, the pellet tapped loose, and then resuspended in 5 ml of cold 0.17 $NH_4Cl$ for 10 min to lyse red blood cells. Chilled DMEM with 20% fetal calf serum is added and the cells pelleted, and then again suspended in 10 ml DMEM supplemented with 20% fetal calf serum.

The myeloma cell lines used for fusion are maintained in stationary suspension cultures in DMEM with high glucose (4.5 g/L) and 20% fetal calf serum, in 5–10% $CO_2$ at a cell concentration between 100,000 and 1,000,000 per ml. The myeloma (plasmacytoma) cell lines can be P3/X63-Ag8, which is a Balb/C plasmacytoma derived from MOPC-21 (Svasti and Milstein, Biochem. J. 128: 427–444, 1972), or a derivative thereof known as FO (Fazekas de St. Groth and Scheidegger, Basle Institute of Immunology, Basle, Switzerland), or 45.6TG1.7, which is a Balb/C line derived from MPC-11 (Margulies et al., Cell 8: 405–415, 1976). All of these lines lack the enzyme hypoxanthine phosphoribosyl transferase (HPRT; E.C. 2.4.2.8) and are thus killed in a selective medium containing hypoanthine, aminopterin, and thymidine (HAT), as described by Littlefield (Science 145: 709–710, 1964).

The spleen cells obtained from the immunized animal are then fused with the plasmacytoma cells by using polyethylene glycol according to an adaptation of the method of Gelfer et al. (Somatic Cell Genetic. 3: 231–236, 1977). For example, a 30% polyethylene glycol solution is made by heating sterile polyethylene glycol 4000 (Merck, molecular weight of about 4,000) (0.5 g Polyethylene glycol+0.05 ml dimethyl sulfoxide (DMSO)+0.5 ml distilled water) and DMEM without serum to 41° C. and mixing 3 ml of polyethylene glycol with 7 ml DMEM without serum, pH 7.4–7.6, and kept at 37° C. until use. Fusions are made at room temperature. The myeloma cells ($10^6$–$10^7$) are washed twice in serum-free medium and then mixed with $1-3\times10^7$ – $1-3\times10^8$ spleen cells in 50 ml conical bottom centrifuge tubes (Falcon 2070). The cells are centrifuged at $250\times g$ for 5 min, and the supernatant fluid is carefully aspirated. An amount of 0.2 ml of the polyethylene glycol preparation is added, and the tube is gently agitated by hand to resuspend the cells. Next, the cells are centrifuged for 3 min at $250\times g$ and again at $400\times g$ for another 3 min, and then kept undisturbed for an additional 3 min. The cells are exposed to polyethylene glycol for about 8 minutes. Thereafter, about 5 ml of serum-free medium is added to the tube, the cells are resuspended gently, and then repelleted by centrifugation at $250\times g$ for 5 min. The supernatant is removed and the cells are suspended in 20 ml of serum-containing medium and incubated at 37° C. in a humidified incubator for 48 hr. before being placed in microplates to which HAT medium is added. Alternatively, the cells are immediately suspended in 30 ml of a medium consisting of DMEM, 10% NCTC 109 medium (Microbiological Associates), 20% fetal calf serum (GIBCO), 0.2 units bovine insulin/ml (Sigma), 0.45 mM pyruvate, 1 mM oxaloacetate, and antibiotics of choice. Thymidine ($1.6\times10^{-5}$ M) and hypoxanthine ($1\times10^{-4}$ M) are added. The cells in this medium are distributed into 6 microplates (Linbro FB 96 TC) with 1 drop (about 50 $\mu$l) per well. The next day 1 drop of the above-specified medium containing thymidine and hypoxanthine, now with aminopterin ($8\times10^{-7}$ M), is added to each well. Two drops of the medium of above is added 6–7 days later and clones appear microscopically between 10 and 20 days. The hypoxanthine-aminopterin-thymidine (HAT) medium can also be added immediately after the fusion, or at a later time. An improvement in the number of hybrids obtained is made when a feeder layer is added to each microwell. Here, human fetal fibroblasts are irradiated with 4500 r, and 1,000–2,000 such cells are added to each well, either the day before the fusion or directly to the fused cells and so dispensed with them into the microwells. After clones have appeared macroscopically, the medium is changed by removing most of the medium and adding fresh medium. After a second change of medium, the medium is left there for at least 4 days and then collected for assays of antibody activity and specificity by conventional assays.

Large amounts of antibody are obtained from spent culture medium harvested from 150 mm plates or roller bottles. The medium is subsequently concentrated by means of a hollow-fiber concentrator (Amicon). Also, antibody is obtained from the ascites fluid of athymic (nude) mice (nu/nu) that were injected 2–3 weeks previously with about 1 billion cloned hybridoma cells. The ascites fluid is diluted with saline by flushing the peritoneal cavity of each mouse with saline, the diluted fluids from each mouse are pooled.

The monoclonal anti-CEA IgG is radiolabeled with I-131 as in Example 1(f).

EXAMPLE 3

Preparation of $^{123}$I-IgG (goat)

Normal goat immunoglobulin G (IgG) (Miles) is affinity purified against cyanogen bromide-linked CEA and labeled with I-123 as in Example 1(f), except that I-123 is substituted for I-131, with proportional changes in the reagents to account for differences in specific activity.

EXAMPLE 4

Preparation of $^{131}$I-anti-CEA-$^{10}$B IgG (a) Anti-CEA IgG prepared according to Examples 1 or 2 is reacted with a 20-fold molar excess of the diazonium salt of 1-(4-aminophenyl)-1,2-dicarba-closo-dodecaborane (12) having a natural abundance of Boron-10 isotope (20%), using the procedure of Hawthorne et al., J. Med. Chem., 15, 449 (1972). The resultant antibody has an average of from 2 to 10 diazolinked carborane residues or from 4 to 20 Boron-10 atoms per antibody molecule.

(b) The anti-CEA-$^{10}$-B of part (a) is radiolabeled with I-131 as in Example 1(f), to introduce an average of from 2.5 to 10 atoms of iodine per antibody molecule.

EXAMPLE 5

Preparation of injectable compositions

Sterile, pyrogen-free solutions are prepared as shown.

(a) A sterile solution containing, per ml:

(1) 10 mg Human Serum Albumin (HSA) (1%, USP, Parke-Davis)
(2) 0.01 M phosphate buffer, pH 7.5 (Bioware)
(3) 0.9% NaCl
(4) 80 μg $^{131}$I-anti-CEA IgG (goat) prepared according to Example 1 (average of about 5 atoms of iodine/molecule, specific activity of about 40 μCi/μg).

The labeled antibody of Example 1 is stored in a solution of (1), (2) and (3) at a concentration of 160 μg/ml and diluted with an equal volume of 1% HSA in phosphate buffered saline (PBS) to prepare this solution.

(b) A sterile solution according to the procedure of part (a) except that it further contains 80 μg/ml of $^{123}$I-IgG as prepared in Example 3. The $^{123}$I-IgG is stored in phosphate buffered saline containing 1% HSA at a concentration of 160 μg/ml. An equal volume of this solution is used in place of 1% HSA in PBS in the procedure of part (a).

(c) A sterile solution according to the procedure of part (b) except that the antibody is the $^{131}$I-anti-CEA IgG (monoclonal) prepared according to Example 2, stored in 1% HSA in PBS at a concentration of 160 μg/ml and having comparable activity.

(d) A sterile solution according to the procedure of part (b) except that the antibody is the $^{131}$I-anti-CEA-$^{10}$B IgG prepared according to Example 4, having an average of 5 diazo-linked carborane residues and 3 atoms of iodine per antibody molecule, and a specific activity of about 24 μCi/μg. The final solution contains 133 μg/ml of the antibody.

EXAMPLE 6

Tumor Localization

Radioiodinated anti-CEA IgG is administered to patients with suspected tumors. The patient is pre-tested for anaphylactic hypersensitivity to goat IgG or myeloma IgG. To block thyroid uptake of I-131 or I-123, Lugol's solution (Purepack) is administered by mouth, 5 drops twice daily for seven days beginning one day before injection of the radioactively labeled antibody.

Localization is effected according to the procedure of Goldenberg et al., N. Eng. J. Med. 298, 1384 (1978), by infusion of a 0.06 ml solution of $^{131}$I-anti-CEA IgG containing $^{123}$I-IgG prepared according to Example 5(b) or 5(c) in 20 ml of sterile physiological saline over a period of from 10 minutes to 45 minutes. No Tc-99m compounds are used, the subtraction technique being adapted in a conventional fashion to discriminate between $^{131}$I and $^{123}$I. Scans are taken immediately and at 2, 8, 12, 24, 48, and 72 hours after injection of the antibody is completed.

Significant localization is seen after 2 hours, with improved resolution with time, tending to plateau between 8 and 24 hours after injection. No additional background $^{123}$I-IgG is added. The CEA-selectivity of this method is comparable to the earlier Goldenberg et al. method, but the resolution, rapidity and convenience is enhanced significantly.

EXAMPLE 7

Tumor Therapy (a) A patient having an ovarian cancer, optionally detected and localized by the procedure of Example 6, is injected by intravenous infusion with 150 mCi of the solution of Example 5(a) in 50 ml of sterile physiological saline. Reduction in tumor size is observed within 20 days. The dose is repeated at intervals adjusted on an individual basis.

(b) A patient having a cervical cancer optionally detected and localized by the procedure of Example 6 is injected with an amount of the solution of Example 5(d) (in 50 ml of sterile physiological saline) sufficient to provide 200 μCi of $^{131}$I activity based on a 70 kg patient weight.

The tumor is precisely localized 12 hours after injection using the procedure of Example 6. A well collimated beam of thermal neutrons is focused on the defined tumor locations. Irradiation with an external neutron beam dose of 400–800 rads, delivered in a period of from 8–20 min, is effected for each tumor locus, and is optionally repeated with administration of the tumor-localizing antibody, with or without the radiolabel, at intervals adjusted on an individual basis, but usually not exceeding a total dose of 3200 rads unless simultaneous external neutron beam therapy is indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method for determining the location of a tumor which either produces or is associated with carcinoembryonic antigen (CEA), which comprises injecting a human subject parenterally with an antibody specific to CEA and radiolabeled with a pharmacologically inert radioisotope capable of detection using a photoscanning device and subsequently scanning the subject with said device to determine the location of the resultant uptake of said labeled antibody by said tumor;

the improvement which comprises concurrently injecting said human subject with normal immunoglobulin from the same or different species as that used to prepare said specific antibody, said normal immunoglobulin being radiolabeled with a different radioisotope of the same element used to label the specific antibody and emitting at an energy capable of independent detection using said photoscanning device, the level of activity of the labeled normal immunoglobulin being used to determine the distribution of background activity due to nontargeted specific antibody, said distribution being subtracted from the total activity of specific antibody whereby the activity of substantially only the targeted tumor-associated antibody is determined.

2. The method of claim 1, wherein the specific anti-CEA antibody is labeled with one of, and the normal immunoglobulin is labled with the other of Iodine-131 and Iodine-123; Indium-111 and Indium-113m; Gallium-67 and Gallium-68; Ruthenium-97 and Ruthenium-103; or Mercury-197 and Mercury-203.

3. The method of claim 1, wherein the specific anti-CEA antibody is labeled with one of Iodine-131 or Iodine-123 and the normal immunoglobulin is labeled with the other of Iodine-131 or Iodine-123.

4. The method of claim 1, wherein the amount of radiolabel introduced into the specific anti-CEA antibody is sufficient to reduce the CEA specific immunoreactivity of said antibody by from 5 to 33%.

5. The method of claim 4, wherein said immunoreactivity is reduced by from 10 to 25%.

6. The method of claim 4, wherein the specific anti-CEA antibody is radiolabeled with Iodine-131 or Iodine-123, an average of at least 2.5 atoms of iodine per antibody molecule being introduced.

7. The method of claim 6, wherein an average of at least 5 atoms of iodine per antibody molecule are introduced by direct chemical substitution.

8. In a method for determining the location of a tumor which either produces or is associated with carcinoembryonic antigen, which comprises injecting a human subject parenterally with an antibody specific to CEA and radiolabeled with a pharmacologically inert radioisotope capable of detection using a photoscanning device and subsequently scanning the subject with said device to determine the location of the resultant uptake of said labeled antibody by said tumor;

the improvement which comprises using as said anti-CEA antibody a substantially monospecific antibody having a CEA-specific immunoreactivity prior to labeling of at least 70% and a cross-reactivity to other antigens of less than 15%, said antibody being radiolabeled to an extent sufficient to reduce its CEA-specific immunoreactivity by from 5 to 33%.

9. The method of claim 8, wherein said substantially monospecific antibody is a monoclonal anti-CEA antibody.

10. The method of claim 8, wherein said substantially monospecific antibody has a CEA-specific immunoreactivity prior to labeling of at least 80% and a cross-reactivity of less than 10%.

11. The method of claim 9, wherein said monoclonal antibody has a CEA-specific immunoreactivity prior to labeling of at least 90% and a cross-reactivity of less than 10%.

12. The method of claim 8, wherein said substantially monospecific anti-CEA antibody is radiolabeled with one of Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18.

13. The method of claim 8, wherein said substantially monospecific anti-CEA antibody is radiolabeled with Iodine-131 or Iodine-123, an average of at least 5 atoms of iodine per antibody molecule being introduced.

14. The method of claim 10, wherein said monoclonal anti-CEA antibody is radiolabeled with Iodine-131 or Iodine-123, an average of at least 5 atoms of iodine per antibody molecule being introduced.

15. The method of claim 8, which further comprises concurrently injecting said subject with normal immunoglobulin from the same or different species as that used to prepare said specific antibody, said normal immunoglobulin being radiolabeled with a different radioisotope of the same element used to label the specific antibody and emitting at an energy capable of independent detection using said photoscanning device, the level of activity of the labeled normal immunoglobulin being used to determine the distribution of background activity due to non-targeted specific antibody, said distribution being subtracted from the total activity of specific antibody whereby the activity of substantially only the targeted, tumor-associated antibody is determined.

16. The method of claim 15, wherein said substantially monospecific antibody is labeled with one of I-131 and I-123, and said normal immunoglobulin is labeled with the other of I-131 and I-123.

17. Substantially monospecific anti-CEA antibody having a CEA-specific immunoreactivity prior to labeling of at least 70% and a cross-reactivity to other antigens of less than 15%, said antibody being radiolabeled with a pharmacologically inert radioisotope capable of detection using a photoscanning device, the extent of radiolabeling being sufficient to reduce said CEA-specific immunoreactivity by from 5 to 33%.

18. The antibody of claim 17, wherein said substantially monospecific anti-CEA antibody is radiolabeled with one of Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18.

19. The antibody of claim 17, wherein said radioisotope is Iodine-131 or Iodine-123, an average of at least 2.5 atoms of iodine per antibody molecule being introduced.

20. The antibody of claim 17, wherein said CEA-specific immunoreactivity is at least 80% and said cross-reactivity is less than 10%.

21. The antibody of claim 20, wherein said radioisotope is Iodine-131 or Iodine-123, an average of at least 5 atoms of iodine per antibody being introduced.

22. The antibody of claim 17 which is a monoclonal anti-CEA antibody.

23. The antibody of claim 22, wherein said radioisotope is Iodine-131 or Iodine-123, an average of at least 5 atoms of iodine per antibody being introduced.

24. An injectable composition which comprises
(a) an antibody specific to carcinoembryonic antigen and radiolabeled with a pharmaceutically inert radioisotope capable of detection using a photoscanning device;
(b) normal immunoglobulin from the same or different species as that used to prepare said specific antibody, said normal immunoglobulin being radiolabeled with a different isotope of the same element used to label the specific antibody and emitting at an energy capable of independent detection using said photoscanning device; and
(c) a pharmaceutically acceptable injection vehicle.

25. The composition of claim 24, wherein the specific anti-CEA antibody is labeled with one of, and the normal immunoglobulin is labeled with the other of Iodine-131 and Iodine-123; Indium-111 and Indium-113m; Gallium-67 and Gallium-68; Ruthenium-97 and Ruthenium-103; or Mercury-197 and Mercury-203.

26. The composition of claim 24, wherein the specific anti-CEA antibody is labeled with one of Iodine-131 or Iodine-123 and the normal immunoglobulin is labeled with the other of Iodine-131 or Iodine-123.

27. An injectable composition which comprises
(a) substantially monospecific anti-CEA antibody having a CEA-specific immunoreactivity prior to labeling of at least 70% and a cross-reactivity to other antigens of less than 15%, said antibody being radiolabeled with a pharmacologically inert radioisotope capable of detection using a photoscanning device, the extent of radiolabeling being sufficient to reduce said CEA-specific immunoreactivity by from 5 to 33%; and (b) a pharmaceutically acceptable injection vehicle.

28. The composition of claim 27, wherein said CEA-specific immunoreactivity is at least 80% and said cross-reactivity is less than 10%.

29. The composition of claim 28, wherein said radioisotope is Iodine-131 or Iodine-123, an average of at least 5 atoms of iodine per antibody being introduced.

30. The composition of claim 27, wherein said antibody is a monoclonal anti-CEA antibody.

31. The composition of claim 30, wherein said radioisotope is Iodine-131 or Iodine-123, an average of at least 5 atoms of iodine per antibody being introduced.

32. A method of tumor radiotherapy, which comprises parenterally injecting into a human subject having a tumor which produces or is associated with carcinoembryonic antigen (CEA) a tumor-reducing amount of an antibody which is specific to CEA and radiolabeled with a pharmacologically inert, radiotherapeutically effective radioisotope; wherein said antibody is substantially monospecific to CEA, having a CEA-specific immunoreactivity prior to labeling of at least 70% and a cross-reactivity to other antigens of less than 15%.

33. The method of claim 32, wherein said antibody is a monoclonal anti-CEA antibody.

34. The method of claim 32, wherein said radioisotope is I-131 and said amount is from 25 to 250 mCi per administration.

35. The composition of claim 27, which further comprises normal immunoglobulin from the same or different species as that used to prepare said specific antibody, said normal immunoglobulin being radiolabeled with a different isotope of the same element used to label the specific antibody and emitting at an energy capable of independent detection using said photoscanning device.

36. A method of tumor radiotherapy, which comprises the steps of parenterally injecting into a human subject having a tumor which produces or is associated with CEA a radiotherapeutically effective amount of an antibody which is specific to CEA and radiolabeled with a pharmacologically inert radioisotope capable of detection with a photoscanning device, said labeled antibody further containing in chemical combination an addend containing at least five atoms of boron with at least a natural abundance of Boron-10 isotope; locating said tumor by scanning the subject with said photoscanning device to determine the location of the resultant uptake of said labeled antibody by said tumor; and directing a beam of thermal neutrons at said tumor location.

37. The injectable composition of claim 24 or 27, wherein said radiolabeled anti-CEA antibody further contains in chemical combination an addend containing at least five atoms of boron with at least a natural abundance of Boron-10 isotope.

38. An antibody which is specific to carcinoembryonic antigen, said antibody being radiolabeled with a pharmacologically inert radioisotope capable of detection with a photoscanning device, said labeled antibody further containing in chemical combination an addend containing at least five atoms of boron with at least a natural abundance of Boron-10 isotope.

39. The antibody of claim 17, wherein said radiolabeled antibody further contains in chemical combination an addend containing at least five atoms of boron with at least a natural abundance of Boron-10 isotope.

* * * * *